(12) United States Patent
Doehner, Jr. et al.

(10) Patent No.: US 6,294,676 B2
(45) Date of Patent: Sep. 25, 2001

(54) PROCESS FOR THE PREPARATION OF 6-(ARYLCARBONYL)-4-OXIMO-DIHYDROBENZOTHIOPYRAN HERBICIDES AND INTERMEDIATES USEFUL THEREIN

(75) Inventors: Robert Francis Doehner, Jr., East Windsor; Thomas Walter Drabb, Trenton, both of NJ (US); Robert Paul Brigance, Levittown, PA (US)

(73) Assignees: American Cyanamid Company, NJ (US); Idemitsu Kosan Co., Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/461,621

(22) Filed: Dec. 15, 1999

Related U.S. Application Data

(63) Continuation of application No. 09/168,124, filed on Oct. 7, 1998, now Pat. No. 6,008,402
(60) Provisional application No. 60/098,829, filed on Sep. 2, 1998, and provisional application No. 60/061,477, filed on Oct. 8, 1997.

(51) Int. Cl.[7] ............. C07D 231/10; C07D 335/04; C07C 321/00
(52) U.S. Cl. ............ 548/375.1; 549/23; 560/9
(58) Field of Search ................. 560/9; 549/23; 548/375.1

(56) References Cited

U.S. PATENT DOCUMENTS

| | | |
|---|---|---|
| 4,919,705 | 4/1990 | Shibata et al. . |
| 4,925,970 | 5/1990 | Brown . |
| 5,468,722 | 11/1995 | Shibata et al. . |
| 5,506,194 | 4/1996 | Nasuno et al. . |
| 5,607,898 | 3/1997 | Nakamura et al. . |
| 5,767,289 | 6/1998 | Nakamura et al. . |

FOREIGN PATENT DOCUMENTS

| | | |
|---|---|---|
| 0 305 529 | 2/1989 | (EP) . |
| 0 629 623 A1 | 12/1994 | (EP) . |
| 96 00247A | 7/1996 | (HU) . |
| WO 95/13275 | 5/1995 | (WO) . |

OTHER PUBLICATIONS

Ramadas, S.R. and Vijaya Krishna, M., Phosporous and Sulfer, 15, 311–315 (1983).
McAndrew, B.A., Journal Chemical Society, Perkin I, 1837–1846 (1979).
Jan. 29, 1999, European Search Report EP 98 30 8167.
Kubota et al, "Preparation of Pyrazoles and Their Use as Herbicides," CA 129 41126, 1998.

*Primary Examiner*—Deborah C. Lambkin
(74) *Attorney, Agent, or Firm*—Finnegan, Henderson, Farabow, Garrett & Dunner, L.L.P.

(57) ABSTRACT

The present invention provides compounds of formula I and processes for the preparation and purification thereof.

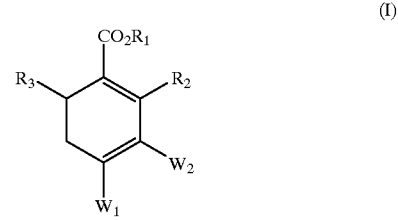

(I)

Compounds of formula I are useful as intermediates in the manufacture of 6-(arylcarbonyl)-4-oximino-dihydrobenzothiopyran herbicidal agents.

6 Claims, No Drawings

PROCESS FOR THE PREPARATION OF 6-(ARYLCARBONYL)-4-OXIMO-DIHYDROBENZOTHIOPYRAN HERBICIDES AND INTERMEDIATES USEFUL THEREIN

This is a continuation of application Ser. No. 09/168,124, filed Oct. 7, 1998, U.S. Pat. No. 6,008,402 and claims the benefit of U.S. provisional application No. 60/098,829, filed Sep. 2, 1998 and No. 60/061,477, filed Oct. 8, 1997, all of which are incorporated herein by reference.

BACKGROUND OF THE INVENTION

Dihydrobenzothiopyran compounds (thiochromans) and 4-oxo-dihydrobenzothiopyran compounds (thiochromanones) and the 4-oxime and 4-alkoxime derivatives thereof are useful intermediates in the preparation of 6-(arylcarbonyl)thiochroman herbicidal agents. Said herbicidal agents and methods for their preparation are described in U.S. Pat. Nos. 4,919,705; 5,468,722 and WO 95/13275. The 6-(arylcarbonyl)thiochromans and derivatives thereof are effective herbicidal agents at low rates of application and demonstrate selective control of noxious weeds en the presence of key economic crops such as corn and rice.

Heretofore, methods to prepare the above-said thiochroman and thiochromanone intermediates required appropriately substituted thiophenol starting materials which may be commercially unavailable and difficult to prepare. The importance of thiochroman and thiochromanone derivatives, particularly as essential intermediates in the manufacture of herbicidal 6-arylcarbonylthiochroman agents, creates a significant need in the art for alternative and effective processes for their manufacture.

SUMMARY OF THE INVENTION

The present invention provides compounds of formula

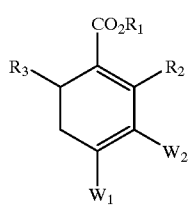
(I)

wherein
- $R_1$ and $R_2$ are each independently $C_1$–$C_4$alkyl;
- $W_1$ is —$SCR_4R_5CR_6R_7COOH$;
- $W_2$ is H or $W_1$ and $W_2$ may together with the carbons to which they are attached form a ring in which $W_1$ and $W_2$ represent

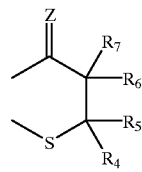

- $R_3$, $R_4$, $R_5$, $R_6$ and $R_7$ are each independently H or $C_1$–$C_4$alkyl;
- Z is O or $NOR_8$; and
- $R_8$ is H, $C_1$–$C_4$alkyl or $C_1$–$C_4$haloalkyl; or when Z is $NOR_8$, the stereoisomers thereof.

Also provided are a process to prepare a thioenol formula Ia compound via the condensation of Hagemann's ester and a β-mercaptopropionic acid and a process to prepare a tetrahydrobenzothiopyran formula Ib compound by the cyclodehydration of the formula Ia thioenol.

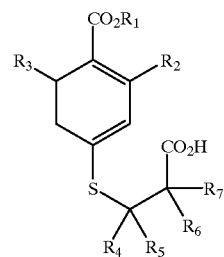
(Ia)

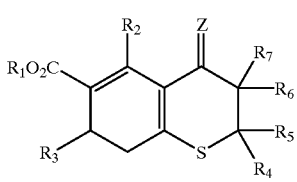
(Ib)

Further provided is the use of the formula I compounds of the invention as intermediates in the manufacture of herbicidal 6-(pyrazol-4-yl)carbonyl-dihydrobenzothiopyran, 4-oxime and 4-alkoxime compounds and in the preparation of dihydrobenzothiopyran intermediates therefor.

Still further provided is a process for the purification and isolation of compounds of formula Ib wherein Z is O.

DETAILED DESCRIPTION OF THE INVENTION

Preferred compounds of formula I are those compounds wherein $R_3$, $R_4$, $R_5$, $R_6$ and $R_7$ are H. Also preferred are compounds of formula I wherein $R_1$ is methyl or ethyl. Further, compounds of formula Ib wherein Z is $NOR_8$ and $R_9$ is H or methyl are preferred.

The term haloalkyl as used in the specification and claims designates an alkyl group $C_mH_{2m+1}$ which may be substituted with 1 to $2m+1$ halogen atoms which may be he same or different. The term halogen designates Cl, Br, I or F.

The compounds of the invention of formula Ib wherein Z is $NOR_9$ (Ib2) include the E and Z stereoisomers shown below.

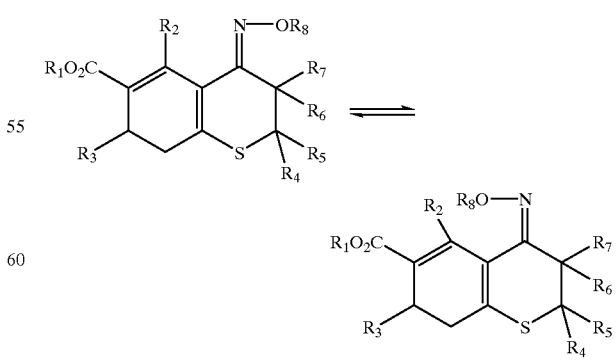

Compounds of the invention exemplary of formula Ia include: ethyl 4-β-carboxyethylthio-2-methyl-1,3- cyclohexadiene-1-carboxylate; methyl 4-β-carboxyethylthio-2-methyl-1,3-cyclohexadiene-1-carboxylate; ethyl 4-β-carboxyethylthio-2-ethyl-1,3-cyclohexadiene-1-carboxylate; methyl 4-β-carboxyethylthio-2-ethyl-1,3-cyclohexadlene-1-carboxylate; and the like.

Compounds of the invention exemplary of formula Ib include: ethyl 5-methyl-4-oxo-2,3,7,8-tetrahydro-4H-1-benzothiopyran-6-carboxylate; ethyl 5-methyl-4-oxo-2,3,7,8-tetrahydro-4H-1-benzothiopyran-6-carboxylate, 4-oxime; ethyl 5-methyl-4-oxo-2,3,7,8-tetrahydro-4H-1-benzothiopyran-6-carboxylate, 4-(0-methyloxime); methyl 5-methyl-4-oxo-2,3,7,8-tetrahydro-4H-1-benzothiopyran-6-carboxylate; methyl 5-methyl-4-oxo-2,3,7,8-tetrahydro-4H-1-benzothiopyran-6-carboxylate, 4-oxime; methyl 5-methyl-4-oxo-2,3,7,8-tetrahydro-4H-1-benzothiopyran-6-carboxylate, 4-O-methyloxime; and the like.

Thiochroman (tetrahydrobenzothiopyran) and thiochromanone (4-oxo-tetrahydrobenzothiopyran) derivatives have heretofore been prepared by the reaction of an appropriate thiophenol substrate with an α,β-unsaturated carboxylic acid, or a 3-halopropionate, followed by cyclodehydration. However, the required appropriate thiophenol starting material may be unavailable commercially and can require up to four synthetic steps to prepare.

It has now been found that thiochromanone derivatives may be prepared from the readily available Hagemann's ester of formula IV. The formula IV ester may be purchased or, alternatively, may be prepared from the easily obtainable simple starting materials of alkyl acetoacetate and formaldehyde.

Surprisingly, the formula IV ester may be condensed with a β-mercapcopropionic acid of formula V to give the thioenol formula Ia compound of the invention. The reaction is shown in flow diagram I wherein $R_1$ and $R_2$ are each independently $C_1$–$C_4$alkyl and $R_3$, $R_4$ $R_5$, $R_6$ and $R_7$ are each independently H or $C_1$–$C_4$alkyl.

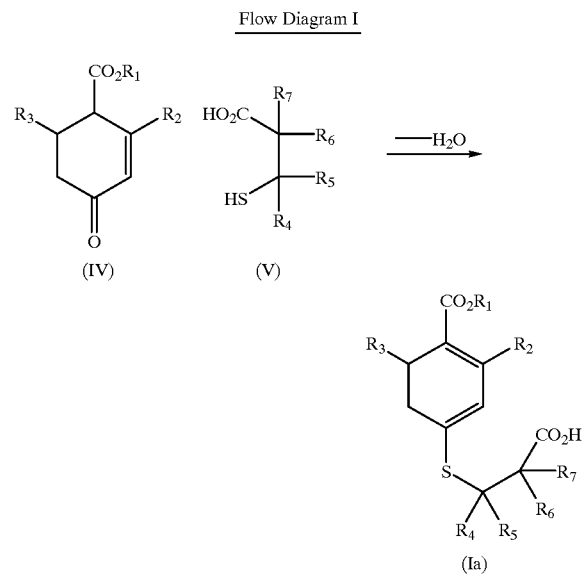

Flow Diagram I

The condensation may be carried out in the presence of a solvent, an acid catalyst and the azeotropic removal of water. Suitable solvents are any inert solvent capable of forming an azeotrope with water such as toluene, benzene, halobenzene, xylene or the like, preferably toluene. Suitable acid catalysts include sulfuric acid, methanesulfonic acid, p-toluenesulfonic acid, pyridinium p-toluenesulfonate, boron trifluoride, pyridinium methanesulfonate and the like, preferably pyridinium methanesulfonate or pyridinium p-toluenesulfonate. Any appropriate water separator, such as a Dean Stark trap may be used to remove the azeotroped water. Increased reaction temperature leads to increased reaction rate and drives the reaction to completion. However, excessively high temperatures may be detrimental and are not required. Preferable reaction temperatures may range from room temperature to the reflux temperature of the solvent, about 25°–200° C., more preferably about 75°–150° C.

Alternatively, the condensation illustrated in flow diagram I may be carried out in the presence of a solvent, an acid catalyst and a dehydrating agent. Suitable dehydrating agents are acetic anhydride, triethyl orthoformate, trimethyl borate, and the like, and mixtures thereof. Solvents suitable for use include toluene, benzene, halobenzene, xylene and the like, preferably toluene. Acid catalysts useful in the condensation include sulfuric acid, methanesulfonic acid, p-toluenesulfonic acid, pyridinium p-toluenesulfonate, boron trifluoride, pyridinium methanesulfonate and the like, preferably pyridinium methanesulfonate or pyridinium p-toluenesulfonate.

The formula Ia thioenol compounds of the invention may be readily converted to 4-oxo-tetrahydrobenzothiopyran compounds of formula Ib1 via a simple single cyclodehydration step as shown in flow diagram II wherein $R_1$, $R_2$, $R_3$, $R_4$, $R_5$, $R_6$ and $R_7$ are as described hereinabove.

Flow Diagram II

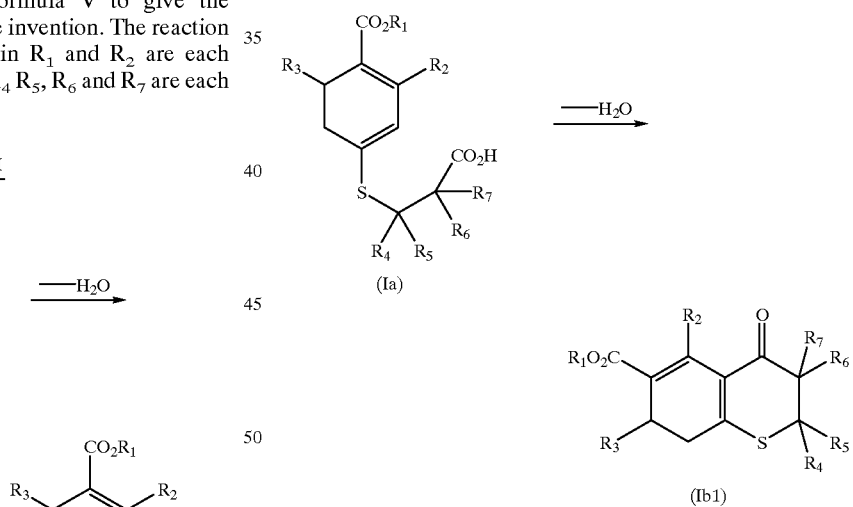

The cyclodehydration may be carried out in the presence of a solvent and a dehydrating agent and optionally in the presence of an acid catalyst. Solvents contemplated for use in the cyclodehydration reaction are any inert solvent which is relatively nonreactive towards water or any of the utilized reagents. Suitable solvents are toluene, benzene, halobenzene, xylene and the like, preferably toluene. Dehydrating reagents particularly suitable for the cyclodehydration reaction shown in flow diagram II are acetic anhydride, trifluoroacetic anhydride, phthaloyl chloride, trifluoroacetyl chloride, and the like. Acid catalysts which optionally may be present include sulfuric acid, methanesulfonic acid, p-toluenesulfonic acid, pyridinium p-toluenesulfonate, boron trifluoride, pyridinium methanesulfonate and the like, preferably methanesulfonic acid. Reaction rate is increased by increased temperatures, however excessively high temperatures may be detrimental and are to be avoided. Suitable reaction temperatures may range from 0° C. to the boiling point of the solvent.

Advantageously, the cyclodehydration of a thioenol compound of formula Ia to form a 4-oxo-tetrahydrobenzothiopyran compound of formula Ib1 may be performed in situ, thereby allowing the formation of said formula Ib1 compound from a formula IV Hagemann's ester in a single reaction vessel, utilizing a common solvent system and acid catalyst.

Compounds of formula Ib1 thus-obtained are frequently tacky, gummy solids which may be very difficult to isolate and purify. Surprisingly, it has now been found that compounds of formula Ib1 may be crystallized by treating said compounds with a solvent mixture of isopropanol and heptane, thus allowing ease of isolation via simple filtration and optimal purity. A preferable solvent mixture is a mixture of about 1:1 volume/volume isopropanol:heptane. Advantageously, the mother liquors obtained from the filtration process may be recycled and used continually to further isolate and purify the formula Ib1 compound.

Those compounds of the invention of formula Ib wherein Z is $NOR_8$ (Ib2) may be prepared by conventional oximation or alkoximation methods such as reacting the formula Ib1 ketone with an oxylamine, $H_2NOR_8$ or a salt thereof in the presence of a polar solvent and an acid acceptor. The reaction is shown in flow diagram III wherein $R_8$ is H, $C_1$–$C_4$alkyl or $C_1$–$C_4$haloalkyl and $R_1$, $R_2$, $R_3$, $R_4$, $R_5$, $R_6$ and $R_7$ are described hereinabove.

The oximation reaction may be accomplished in a polar solvent such as an aliphatic alcohol, acetic acid, or the like, or combinations thereof, in the presence of an acid acceptor such as pyridine, sodium acetate, or the like. Reaction temperatures are directly proportional to reaction rate. Therefore, increased reaction temperatures lead to increased reaction rate. However, excessively high reaction temperatures may lead to decomposition and undesirable side reactions. Suitable reaction temperatures range from room temperature to the reflux temperature of the solvent, i.e. about 25° C. to the boiling point of the solvent.

The present invention further provides the use of tne compounds of formula I in a process to prepare imcortant dihydrobenzothiopyran intermediates of formula III in he manufacture of 6-(arylcarbonyl)thiochromanone herbicida agents. Advantageously, the inventive process orovides a route to the key formula III dihydrobenzothiopyran intermediates starting from the readily available and easily obtainable Hagemann's ester compound of formula IV.

In accordance with the invention dihydrobenzothiopyran intermediate compounds of formula III may be effectively prepared by condensing a formula IV ester with the appropriate β-mercaptopropionic acid of formula V to give a thioenol compound of formula Ia; cyclodehydrating said thioenol to give a 4-oxo-tetrahydrobenzothiopyran compound of formula Ib1; reacting said formula Ib1 compound with an oxylamine, $H_2NOR_8$, or a salt thereof to give the 4-oximinotetrahydrobenzothiopyran compound of formula Ib2; and aromatizing said formula Ib2 compound to give the desired formula III dihydrobenzothiopyran.

Optionally, the formula Ib1 compound may be aromatized to give a formula VI 4-oxo-dihydrobenzothiopyran compound; and said formula VI compound may be reacted with an oxylamine, $H_2NOR_8$, or a salt thereof to give the desired formula III dihydrobenzothiopyran. The process of the invention is shown in flow diagram IV wherein $R_1$, $R_2$, $R_3$, $R_4$, $R_5$, $R_6$, $R_7$ and $R_8$ are described hereinabove.

Flow Diagram III

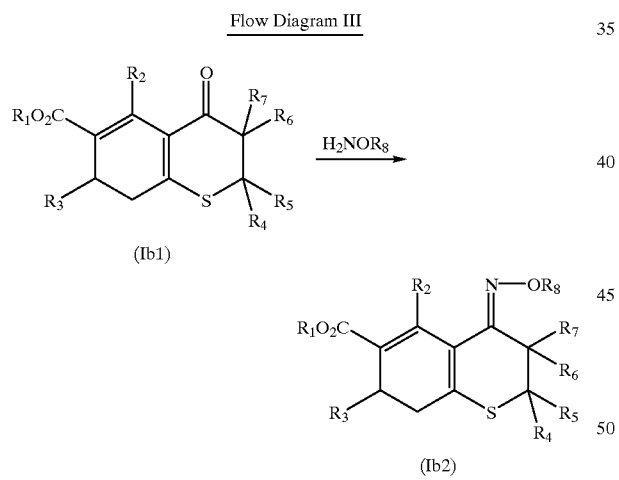

Flow Diagram IV

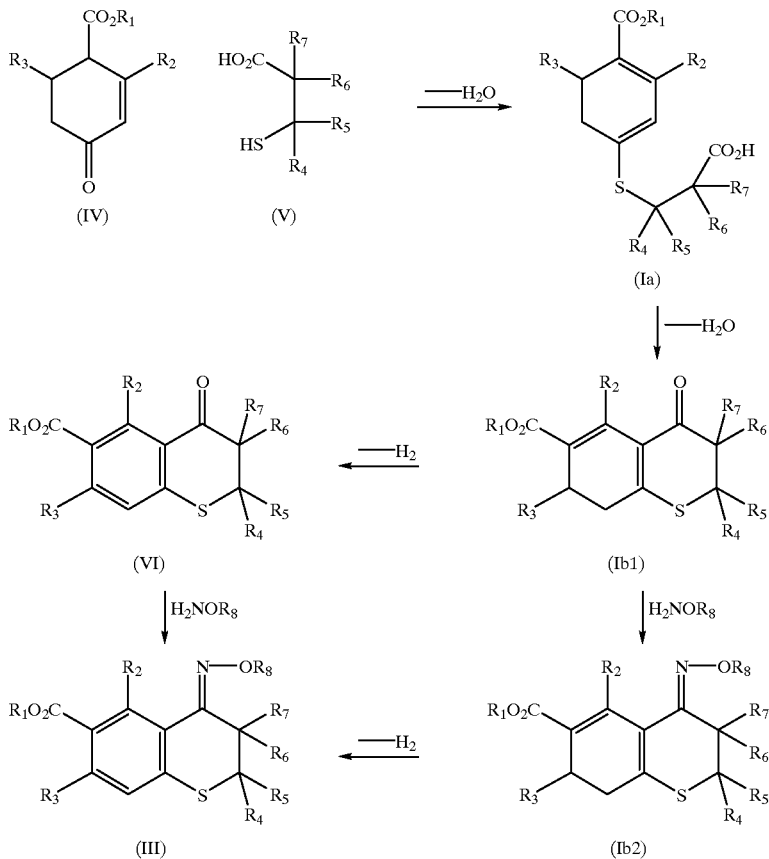

Aromatization of formula Ib1 to formula VI, or formula Ib2 to formula III, may be accomplished by a variety of oxidizing agents such as bromine, dichloro-dicyano-parabenzoquinone (DDQ), sulfur, or the like, in the presence of a solvent such as methylene chloride, chloroform, toluene, acetic acid, or the like, or mixtures thereof. Alternatively, aromatization may be performed by using conventional dehydrogenation techniques such as heating in the presence of a catalyst such as palladium on carbon (Pd/C) and a solvent, optionally in the presence of a hydrogen acceptor. Hydrogen acceptors include conventional hydrogen acceptors such as any olefin capable of reduction, e.g. maleic acid, cyclohexane, cyclohexadione and the like.

The compounds of formula III are useful as key intermediates in the manufacture of 6-[(pyrazol-4-yl)carbonyl]dihydrobenzothiopyran herbicidal agents of formula VII

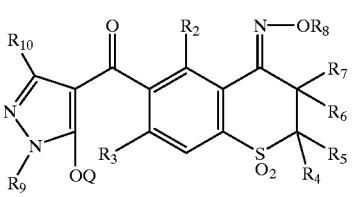

(VII)

wherein
$R_2$ and $R_9$ are each independently $C_1$–$C_4$alkyl;
$R_3$, $R_4$, $R_5$, $R_6$, $R_7$ and $R_{10}$ are each independently H or $C_1$–$C_4$ alkyl;

$R_8$ is H, $C_1$–$C_4$alkyl or $C_1$–$C_4$haloalkyl;
Q is H or $SO_2R_{11}$; and
$R_{11}$ is $C_1$–$C_6$alkyl or phenyl optionally substituted with one to three halogen, $NO_2$, $C_1$–$C_4$alkoxy or $C_1$–$C_4$alkyl groups; or
the tautomers or the stereoisomers thereof.

It has now been found that the formula VII herbicidal agents may be prepared from readily available and easily obtainable starting materials in a cost effective and efficient process of manufacture. In accordance with the process of the invention the formula VII compound may be prepared by condensing an ester of formula IV with a β-mercaptopropionic acid of formula V to form a thioenol compound of formula Ia; cyclodehydrating the formula Ia thioenol to form a tetrahydrobenzothiopyran compound of formula Ib1; reacting the formula Ib1 compound with an oxylamine, $H_2NOR_8$ or a salt thereof, to form the corresponding oxime derivative of formula Ib2; aromatizing said formula Ib2 compound to give the dihydrobenzothiopyran intermediate of formula III; oxidizing the formula III intermediate to give the 1,1-dioxide compound of formula VIII; hydrolyzing said formula VIII compound to give the corresponding 6-carboxylic acid of formula IX; and reacting said formula IX carboxylic acid with a 5-hydroxypyrazole of formula X in the presence of a base and a dehydrating agent to give the 6-(pyrazolylcarbonyl)dihydrobenzothiopyran product compound of formula VIIa wherein Q is hydrogen; or, for compounds of formula VIIb wherein Q is $SO_2R_{11}$, reacting the compound of formula VIIa with a sulfonyl chloride, $R_{11}SO_2Cl$, to give the desired VIIb compound.

Optionally, the formula III intermediate may be prepared by reversing the sequence of the oximation and aromatization steps. The complete reaction sequence is shown in flow diagram V wherein $R_1$, $R_2$, $R_3$, $R_4$, $R_5$, $R_6$, $R_7$, $R_8$, $R_9$, $R_{10}$ and $R_{11}$ are described hereinabove.
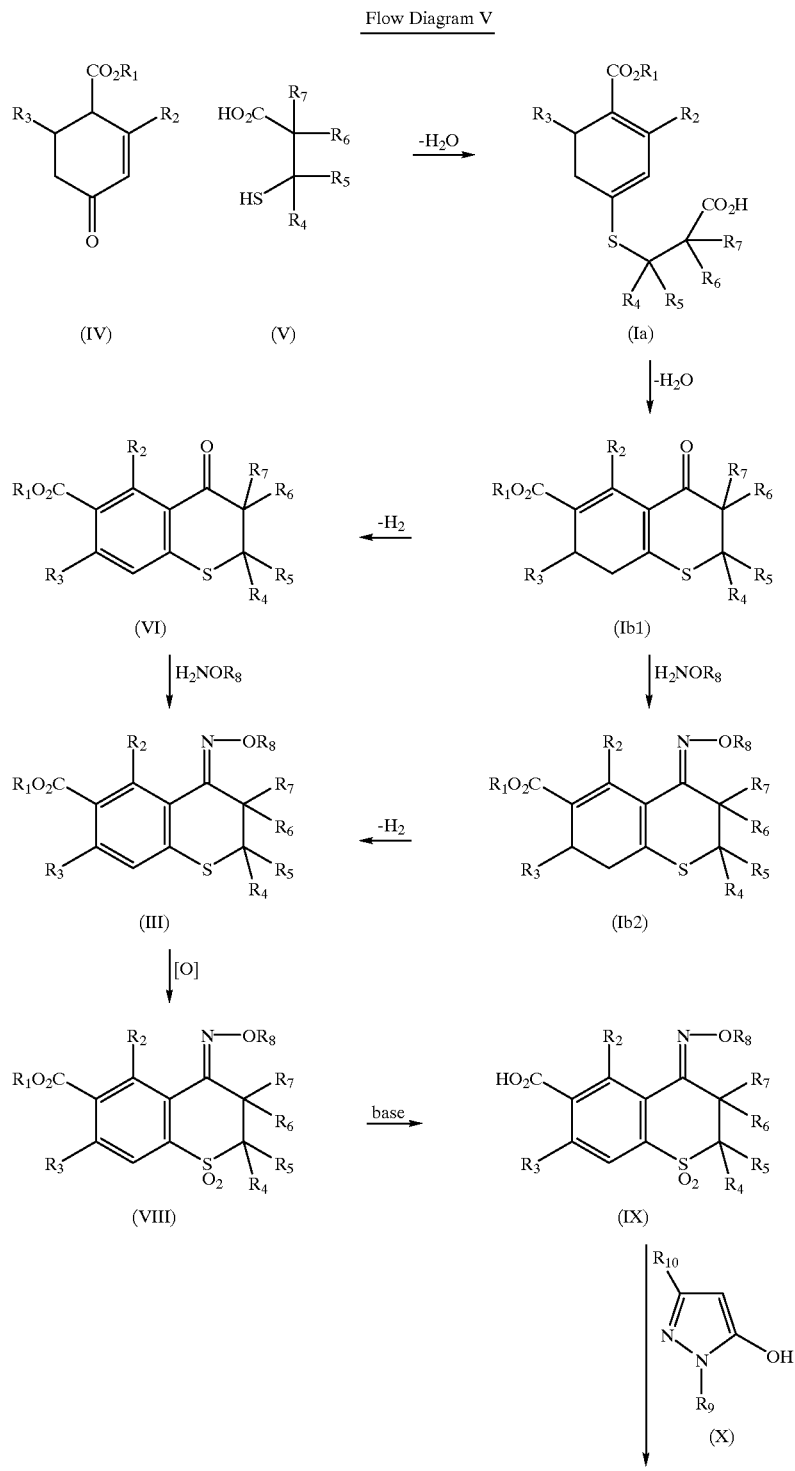
Flow Diagram V

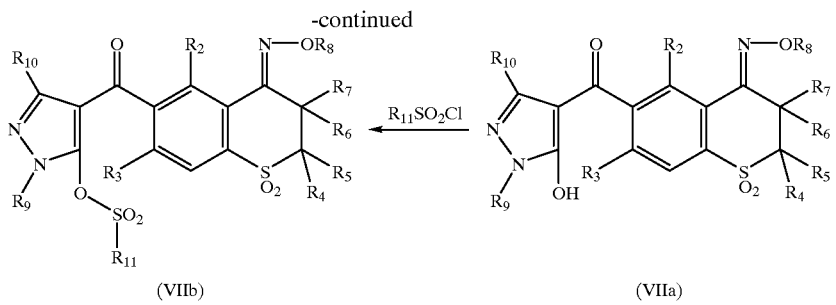

(VIIb)   (VIIa)

The herbicidal agents of formula VIIa and formula VIIb and their preparation from intermediates of formula III are described in WO 95/13275. The oxidation and hydrolysis steps described above may be accomplished using conventional methods such as hydrogen peroxide oxidation and simple base hydrolysis techniques. The coupling of the hydroxypyrazole compound of formula X and the subsequent rearrangement to the desired compound formula VIIa may be performed using conventional methods such as those described in WO 95/13275, i.e. in the presence of a base and a dehydrating agent. Similarly, the sulfonation of formula VIIa with a sulfonyl chloride, $R_{11}SO_2Cl$, to give the desired formula VIIb compound may be accomplished according to conventional methods.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

The term $^1$NMR designates proton nuclear magnetic resonance.

EXAMPLE 1

Preparation of Ethyl 4-β-carboxyethylthio-2-methyl-1,3-cyclohexadiene-1-carboxylate

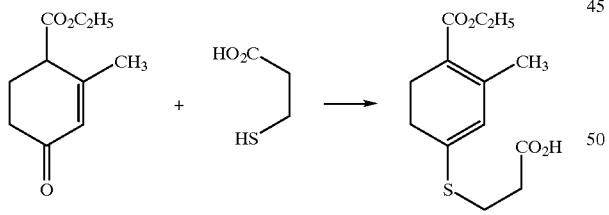

Method A

A solution of ethyl 2-methyl-4-oxo-2-cyclohexenecarboxylate (200 g, 1.1 mole), β-mercaptopropionic acid (104.6 g, 0.99 mole) and p-toluenesulfonic acid hydrate (1.5 g, 0.0079 mole) in toluene is heated at reflux temperatures, under $N_2$, using a Dean Stark trap for 18 hours, cooled and concentrated in vacuo to give a residue. The residue is crystallized in 2:1 hexanes:ether to give the title product as a yellow solid, 135 g (45% yield). A small sample was recrystallized from ethyl acetate/hexane to give a pale yellow solid, mp 96°–97° C., identified by $^1$HNMR and mass spectral analyses.

Method B

A solution of ethyl 2-methyl-4-oxo-2-cyclohexenecarboxylate (42.7 g, 0.23 mole), trimethylborate (10.4 g, 0.10 mole), acetic anhydride (30.7 g, 0.30 mole) and β-mercaptopropionic acid (24.2 g, 0.23 mole) in toluene is stirred at 15° C., treated with 20 drops of methanesulfonic acid and stirred at ambient temperatures for 18 hours. The resultant reaction mixture is partitioned between toluene and dilute aqueous ammonia. The phases are separated and the organic phase is concentrated in vacuo to give an oil residue, 65.5 g, $^1$HNMR analysis of the residue shows the title product as the major component, also present are toluene and starting cyclohexenecarboxylate.

EXAMPLE 2

Preparation of Ethyl 5-methyl-4-oxo-2,3,7,8-tetrahydro-4H-1-benzothioyran-6-carboxylate

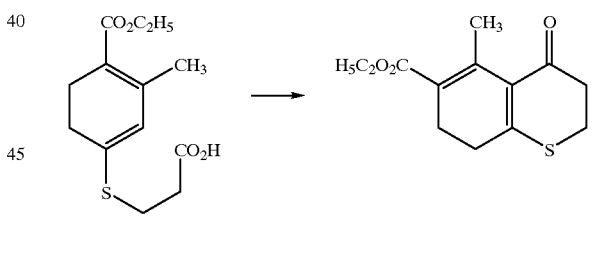

A mixture of ethyl-4-β-carboxyethylthio-2-methyl-1,3-cyclohexadiene-1-carboxylate (121.3 g, 0.449 mole) in toluene is stirred at 200° C., treated sequentially with 5.0 ml methanesulfonic acid and portionwise over a 5 minute period with trifluoroacetic anhydride (94.3 g, 0.449 mole) and allowed to stir at ambient temperatures for 18 hours. The resultant reaction mixture is quenched with a 1:1 mixture of ethyl acetate and water and stirred for 15 minutes. The phases are separated. The organic phase is washed with water and concentrated in vacua to give a residue. Crystallization of the residue from isopropanol/heptane affords the title product as a yellow solid, 90.1 g, (79.5% yield) , mp 99°–100° C., identified by $^1$HNMR and mass spectral analyses.

EXAMPLE 3

Preparation of Ethyl 5-methyl-4-oxo-2,3,7,8-tetrahydro-4H-1-benzothiopyran-6-carboxylate

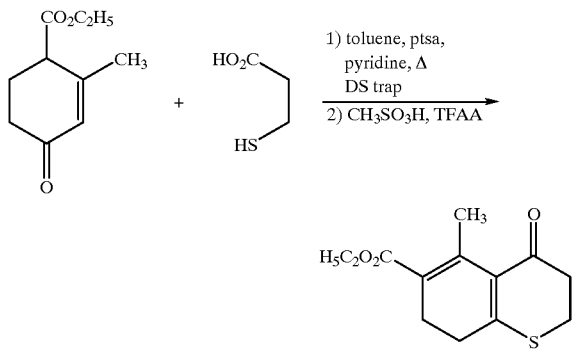

A mixture of ethyl 2-methyl-4-oxo-2-cyclohexenecarboxylate (2.0 kg, 91.2%, 10.98 moles), β-mercaptopropionic acid (1.165 kg, 10.98 moles), p-toluenesulfonic acid (ptsa) monchydrate (0.710 kg, 3.73 moles) and pyridine (0.304 kg, 3.84 moles) in toluene is heated to reflux temperature, heated at reflux temperatures for 7 hours using a Dean Stark trap for removal of water, allowed to cool to room temperature over a 17 hour period, cooled to 50° C., treated with trifluoroacetic anhydride (TFAA) (2.306 kg, 10.98 moles) at 50°–12° C., treated with methanesulfonic acid (0.053 kg, 0.55 moles), allowed to warm to room temperature, held at room temperature until reaction is complete by HPLC analysis and quenched with water. The phases are separated. The organic phase is washed with water and distilled to remove the toluene. The remaining pot residue is treated with isopropyl alcohol (1.89 kg), cooled to 45° C., treated with heptane (1.65 kg), and cooled to room temperature. The resultant mixture is filtered and the filtercake is washed sequentially with a 1:1 isopropanol:heptane mixture (0.735 kg) and heptane (1.37 kg). The washed filtercake is dried in vacuo to give he title product as a white crystalline solid, 0.931 kg (36% yield) 98.4% purity, identified by HPLC analysis.

EXAMPLE 4

Preparation of Substituted 4-oxo-2,3,7,8-tetrahydro-4H-1-benzothioyran-6-carboxylate

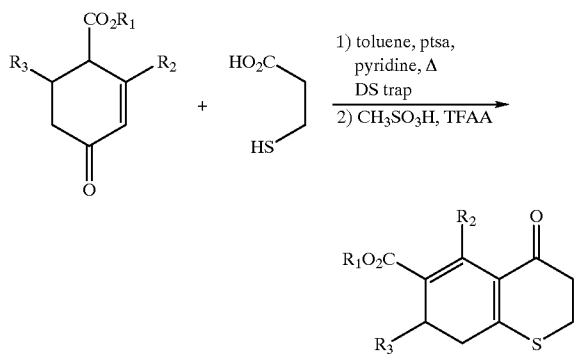

A mixture of substituted 4-oxo-2-cyclohexene-1-carboxylate (1.1 mole), β-mercaptopropionic acid (1.0 mole), p-toluenesulfonic acid hydrate (ptsa) (0.20 mole) and pyridine (0.2 mole) in toluene is heated at reflux temperatures using a Dean Stark (DS) trap for 3 hours. The resultant solution is diluted with toluene, cooled to 10° C., treated sequentially with methanesulfonic acid (0.0625 mole) and trifluoroacetic anhydride (TFAA) (1.0 mole) over a 5 minute period, stirred for 18 hours (the reaction temperature is allowed to rise to 21° C.), quenched with water and stirred for 5 minutes. The phases are separated. The organic phase is washed with water and concentrated in vacua to give a residue. Crystallization of the residue affords the title product.

Using essentially the same procedure described above, the compounds shown below are obtained and identified by $^1$HNMR and mass spectral analyses.

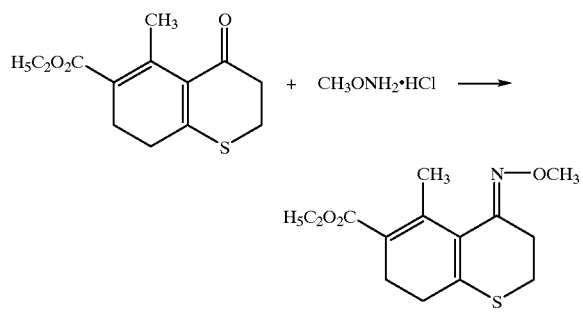

| $R_1$ | $R_2$ | $R_3$ | mp ° C. | % yield |
|---|---|---|---|---|
| $C_2H_5$ | $CH_3$ | H | 99–100 | 56 |
| $CH_3$ | $CH_3$ | H | 138–140 | 16 |

EXAMPLE 5

Preparation of Ethyl 5-methyl-4-oxo-2,3,7,8-tetrahydro-4H-1-benzothiopyran-6-carboxylate, 4-(O-methyloxime)

A mixture of ethyl 5-methyl-4-oxo-2,3,7,8-tetrahydro-4H-1-benzothiopyran-6-carboxylate (106 g, 0.42 mole), 151 g of 25–30% aqueous methoxylamine hydrochloride, 50 ml of pyridine, 500 ml of toluene and 500 ml of ethanol is stirred at reflux temperature for 2 hours, cooled and concentrated in vacuo to give a residue. The residue is partitioned between ethyl acetate and dilute aqueous hydrochloric acid. The organic phase is separated, washed with water and concentrated in vacuo to give a second residue. This residue is crystallized from hexanes to give the title product as a white solid, 37.6 g (32% yield), mp 65°–67° C., identified by $^1$HNMR, and mass spectral analyses.

EXAMPLE 6

Preparation of Ethyl 5-methyl-4-oxo-2,3,7,8-tetrahydro-4H-1-benzothiopyran-6-carboxylate, 4-oxime

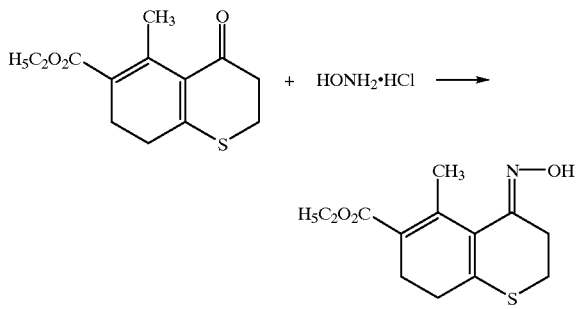

A mixture of ethyl 5-methyl-4-oxo-2,3,7,8-tetrahydro-4H-1-benzothiopyran-6-carboxylate (156 g, 0.619 mole), hydroxylamine hydrochloride (43 g, 0.619 mole), 100 ml of pyridine in 1.0 L of absolute ethanol is stirred at reflux temperature for 18 hours, cooled and concentrated in vacuo to give a residue. The residue is partitioned between dilute aqueous NaCl and an ethyl acetate/methanol mixture. The resultant phase mixture is acidified to pH 1 with concentrated hydrochloric acid. After mixing, the phases are separated and the organic phase is concentrated in vacuo to give a second residue. This residue is slurried in diethyl ether and filtered to afford the title product as an off-white solid, 110 g (66.5% yield) mp 139°–142° C., identified by $^1$HNMR and mass spectral analyses.

EXAMPLE 7

Preparation of Ethyl 2,3-dihydro-5-methyl-4-oxo-4H-1-benzothiopyran-6-carboxylate, 4-(O-methyloxime)

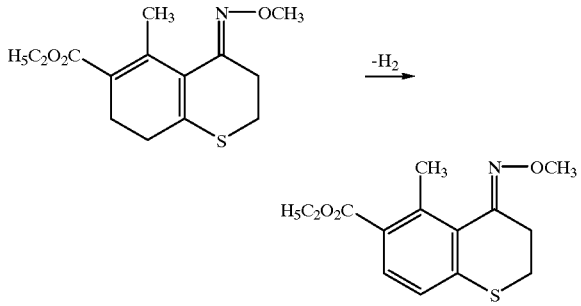

Method A

A solution of ethyl 5-methyl-4-oxo-2,3,7,8-tetrahydro-4H-1-benzothiopyrano-6-carboxylate, 4-(0-methyloxime) (100 g, 0.356 mole) in a 1:1 mixture of methylene chloride and chloroform is stirred at 50° C., treated dropwise with a solution of bromine (56.5 g, 0.353 mole) in methylene chloride over a 30 minute period, stirred at room temperature for 16 hours and heated at reflux temperature for 5 hours. (The liberated hydrogen bromide gas is scrubbed during the entire procedure.) The reaction mixture is cooled and concentrated in vacuo to give a residue. The residue is partitioned between ethyl acetate and dilute aqueous ammonia. The phases are separated and the organic phase is washed with dilute aqueous NaHSO$_3$ and concentrated in vacuo to afford an oil residue. $^1$HNMR analysis of the residue shows the title product as the major component.

Method B

A mixture of ethyl 5-methyl-4-oxo-2,3,7,8-tetrahydro-4H-1-benzothiopyran-6-carboxylate, 4-(0-methyloxime) (2.8 g, 0.01 mole), 7 ml of acetic acid and 0.7 g of 50% aqueous hydrogen peroxide is stirred at room temperature overnight, treated, with cooling, with 0.82 g acetyl chloride and stirred at ambient temperatures for 1 hour. Thin layer chromatographic analysis shows the title product as the major component.

EXAMPLE 8

Preparation of Ethyl 2,3-dihydro-5-methyl-4-oxo-4H-1-benzothiopyran-6-carboxylate

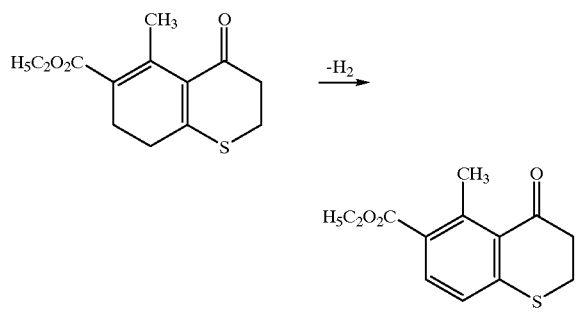

A mixture of ethyl 5-metyl-4-oxo-2,3,7,8-tetrahydro-4H-1-benzothiopyrano-6-carboxylate (25 g, 0.099 mole) and 7 g of 5% Pd/C catalyst in 100 ml of cymene is heated at reflux temperature (about 175° C.) for 24 hours, cooled to 80° C. and filtered. The catalyst filtercake is washed with toluene. The filtrates are combined and concentrated in vacuo to afford the title product, 25.9 g, 90% purity by $^1$HNMR analysis (94% yield)

What is claimed is:
1. A compound of formula I

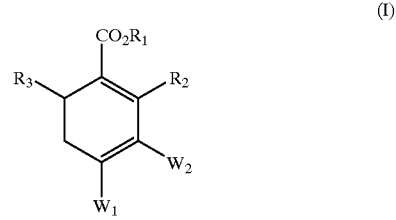

wherein $R_1$ is $C_1$–$C_2$ alkyl;

$R_2$ is $CH_3$ $W_1$ is —$SCR_4R_5CR_6R_7COOH$;

$W_2$ is H or $W_1$ and $W_2$ may together with the carbons to which they are attached form a ring in which $W_1$ and $W_2$ represent

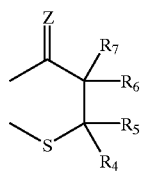

$R_3$, is H or $CH_3$,
$R_4$, $R_5$, $R_6$ and $R_7$ are each independently H
Z is O or $NOR_8$; and
$R_8$ is H, or $CH_3$; or
when Z is $NOR_8$, the steroisomers thereof.

2. The composition of claim 1 which is ethyl 4-β-carboxyethylthio-2-methyl-1,3-cyclohexadiene-1-carboxylate.

3. The composition of claim 1 which is ethyl 5-methyl-4-oxo-2,3,7,8-tetrahydro-4H-1-benzothiopyran-6-carboxylate.

4. The composition of claim 1 which is methyl 5-methyl-4-oxo-2,3,7,8-tetrahydro-4H-1-benzothiopyran-6-carboxylate.

5. The composition of claim 1 which is ethyl 2,3-dihydro-5-methyl-4-oxo-4H-1-benzothiopyran-6-carboxylate, 4-(O-methyloxime).

6. The composition of claim 1 which is ethyl 2,3-dihydro-5-methyl-4-oxo-4H-1-benzothiopyran-6-carboxylate.

* * * * *